(12) United States Patent
Barger et al.

(10) Patent No.: US 6,255,270 B1
(45) Date of Patent: Jul. 3, 2001

(54) CLEANING AND DISINFECTING COMPOSITIONS WITH ELECTROLYTIC DISINFECTING BOOSTER

(75) Inventors: Bruce Barger, West Chester; Thomas James Wierenga, Cincinnati, both of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/011,516

(22) PCT Filed: Jul. 29, 1996

(86) PCT No.: PCT/US96/12191

§ 371 Date: Apr. 12, 1999

§ 102(e) Date: Apr. 12, 1999

(87) PCT Pub. No.: WO97/06237

PCT Pub. Date: Feb. 20, 1997

Related U.S. Application Data

(60) Provisional application No. 60/002,056, filed on Aug. 9, 1995.

(51) Int. Cl.$^7$ ............................... C11D 1/75; C11D 1/62; C11D 3/04; C11D 3/30

(52) U.S. Cl. .................. 510/244; 510/188; 510/199; 510/214; 510/215; 510/243; 510/433; 510/434; 510/503; 510/504

(58) Field of Search ................................ 510/188, 199, 510/214, 215, 243, 244, 433, 434, 503, 504; 134/42

(56) References Cited

U.S. PATENT DOCUMENTS

| | | | |
|---|---|---|---|
| 5,616,781 | * 4/1997 | Sajic et al. | 510/221 |
| 5,691,291 | * 11/1997 | Wierenga et al. | 510/214 |
| 5,977,054 | * 11/1999 | Wierenga | 510/503 |

FOREIGN PATENT DOCUMENTS

| | | | |
|---|---|---|---|
| 1945292 | * 5/1971 | (DE) | . |
| 161811 | * 11/1985 | (EP) | . |
| WO 95/07335 | * 5/1971 | (WO) | . |

* cited by examiner

*Primary Examiner*—Gregory DelCotto
(74) *Attorney, Agent, or Firm*—Jason J. Camp

(57) ABSTRACT

Mildly acidic liquid hard surface cleaning concentrated compositions comprise: a) from 0.5 to 40 parts of an amine oxide detergent; preferably 1 to 25 parts; b) from 1 to 30 parts of a quaternary disinfectant (quat); preferably 2 to 16 parts; c) an effective amount of an acidifying agent; preferably 0.05 part to 10 parts; and d) an effective amount of an electrolytic disinfecting booster; preferably 0.5 to 12 parts; wherein said compositions have a pH of from 3 to less than 7 and wherein when used the concentrated compositions are diluted with water at a ratio of concentrate to water of 1:1 to 1:600, preferably 1:30 to 1:260 by volume, to provide superior, no-rinse ready-to-use cleaning and disinfecting compositions.

17 Claims, No Drawings

CLEANING AND DISINFECTING COMPOSITIONS WITH ELECTROLYTIC DISINFECTING BOOSTER

CROSS-REFERENCE TO RELATED APPLICATIONS

This application is a 371 of International Application PCT/US96/12191, with an international filing date of Jul. 29, 1996, which claims the benefit of U.S. Provisional Application Ser. No. 60/002,056 filed Aug. 9, 1995.

FIELD OF THE INVENTION

This invention relates mildly acidic amine oxide cleaners containing a quat disinfectant.

BACKGROUND OF THE INVENTION

The use of amine oxide surfactants in cleaning compositions is known. Amine oxides are commonly used as cosurfactants to boost and maintain suds formation in laundry, shampoo, and dishwashing detergent compositions. Amine oxides have been used in hard surface cleaners such as acidic toilet bowl cleaners (pH of 2 or less), dishwashing liquids containing occlusive emollients (pH of 4 to 6.9), and selected non-acidic (neutral to alkaline) hard surface cleaners. In non-acidic hard surface cleaners, amine oxide detergent surfactants are essentially non-ionic ($pK_a$ between about 4 and about 6). These nonionic amine oxides provide good cleaning properties and leave little or no visible residue on hard surfaces when they dry.

Quats U.S. Pat. No. 5,435,935, issued to Kupneski, Jul. 25, 1995, herein incorporated by reference, disclose the use of quaternary ammonium (quats) compounds in alkaline liquid hard surface cleaning compositions.

Non-acidic hard surface cleaners containing amine oxides will stain or discolor vinyl (polyvinyl chloride) surfaces. The staining amounts to a light yellow to dark brown discoloration of the vinyl. Staining will also occur on waxed vinyl surfaces where areas of wax are worn thin or are chipped away so that the amine oxide can come in direct contact with the vinyl.

Co-pending and commonly assigned, U.S. patent application Serial No. 08/412,622 (P&G Case 4980R), Wierenga, discloses a mildly acidic hard surface cleaning composition containing amine oxide surfactant with quaternary ammonium disinfectants (quats). However, the compositions, per se, at acidic pH's are incompatible with quaternary ammonium disinfectants in that the quats loose their ability to disinfect.

It is therefore an object of the present invention to provide a hard surface cleaning composition containing mildly acidic amine oxide detergent surfactants that will disinfect and clean with minimal or no vinyl staining.

Another object of the invention to provide such a composition which will disinfect and not leave a visible residue on cleaned surfaces.

It is also an object of this invention to provide a process for cleaning vinyl surfaces using such a composition.

SUMMARY OF THE INVENTION

The compositions of this invention provide a superior combination of cleaning, disinfecting and waxed floor finish compatibility over the state of the art compositions. The preferred compositions are mildly acidic liquid hard surface cleaning compositions comprising:

a) an amine oxide detergent;
b) a quaternary disinfectant (quat);
c) an acidifying agent; and
d) an effective amount of an electrolytic disinfecting booster.

Preferred are ready to use compositions that have a pH of from 3 to less than 7 and from 40 ppm to about 12,500 ppm of amine oxide detergent and from about 50 ppm to about 1500 ppm, preferably at least 500 ppm of quat.

Also disclosed are concentrated hard surface cleaning compositions. The concentrated compositions are formulated to be used as is or diluted with an aqueous carrier at a level of 1:1 up to 1:600. The preferred ratio level is from 1:10 to 1:600 by volume or by weight, more preferably from 1:20 to 1:300, most preferably 1:30 to 1:260. These concentrated compositions of this invention preferably have from about 0.5 to about 40 parts, more preferably 1 to 30 parts, most preferably 1 to 25 parts of an amine oxide detergent surfactant; from about 1 part to about 25 part, preferably 1 to 20 parts, and more preferably 2–16 parts of a quaternary disinfectant; an effective amount, preferably from 0.05 parts to 10 parts, more preferably 0.5 to 5 parts, of an acidifying agent having a $pK_a$ of less than about 6.0; and an effective amount, from 0.05 to 12 parts, preferably 0.2 to 8 parts, and most preferably from 0.2 to 2 parts of an electrolytic disinfecting booster; whereby when said concentrated compositions are mixed with a predetermined amount of water to provide ready to use compositions. The preferred specific gravity of the concentrated liquids of this invention is from 0.9 to 1.1.

The compositions contain enough acidifying agent to protonate at least about 10% of the amine oxide and also provide a dilute composition pH of between about 3 and 7, preferably from 4 to 6. These liquid hard surface cleaning and disinfecting compositions have excellent disinfecting and cleaning properties. They are wax safe. They can be no-rinse compositions. They do not leave a visible residue when they dry. They cause minimal or no staining of vinyl surfaces. Also disclosed is a method for disinfecting and cleaning vinyl surfaces using the liquid compositions. Also disclosed are preferred concentrated compositions from which mildly acidic dilute liquid compositions can easily be obtained by adding an aqueous liquid.

The present invention also embodies a non-liquid formulation from which the liquid composition can be derived. The non-liquid formulation is essentially the liquid composition wherein the amount of the aqueous carrier liquid is reduced (e.g., gel) or essentially eliminated (e.g., granules).

In its method aspect, the present invention relates to a method for disinfecting and cleaning vinyl surfaces using the liquid compositions herein. In accordance with the method, the liquid compositions are applied to a vinyl surface, wiped with a porous material, and allowed to dry.

DETAILED DESCRIPTION OF THE INVENTION

Mildly acidic dilute and concentrated liquid compositions of the present invention comprise: 1) an amine oxide detergent surfactant, 2) an acidifying agent, 3) a quaternary ammonium disinfectant, 4) electrolytic disinfecting booster and 5) an aqueous carrier liquid. The liquid compositions can be used to clean hard surfaces in diluted or undiluted form. The diluted form is preferred because no rinsing is required. Rinsing is desirable if concentrated compositions are used on hard surfaces. To disinfect hard surfaces, the product must provide at least 500 to 600 ppm of quat. To sanitize the product must provide at least about 50 ppm quat, preferably at least 100 ppm quat.

A preferred concentrated composition of this invention comprises: about 1 to 25 parts amine oxide surfactants; about 2 to 16 parts quaternary ammonium chloride; optionals about 1–3 parts EDTA; about 0.2 to 2 parts phosphoric acid; about 0.2 to 2 potassium chloride; and balance water. The pH is preferably adjusted with HCl or phosphoric acid or mixtures thereof to a pH of from 3 to 6.

The liquid compositions can be used as no-rinse hard surface cleaners on floors, walls, toilets, etc. It was found that non-acidic liquid disinfecting and cleaning compositions containing amine oxides will stain vinyl surfaces. The liquid compositions of the present invention, however, will cause minimal or no vinyl staining. Moreover, the liquid compositions have excellent disinfecting and cleaning properties and will leave little or no visible residue when they dry.

The ppm as used herein are ppm by weight of ready to use liquid composition. Weight ppm and volume ppm are about the same since the concentrated compositions of this invention have specific gravities of about 1. Some concentrated compositions have specific gravities that vary slightly but they are considered within the scope of the claimed invention in view of this disclosure. The parts of the concentrates are by weight; but when diluted to provide the ready to use liquid cleaners, ppm by volume can be used to reflect the degree of dilution.

As used herein, "electrolytic disinfecting booster" is coined to mean any electrolytic chemical that will increase the disinfecting efficacy of the compositions of this invention.

As used herein, "mildly acidic" means a pH above about 3.0 and below 7.0. All pH values herein are measured in aqueous systems at 25° C. (77° F.).

As used herein, "vinyl" means material or surfaces containing polyvinyl chloride. Such material or surfaces can be waxed or unwaxed.

As used herein, "non-liquid" means granular, powder or gel formulations which can be diluted with the aqueous carrier liquid described hereinafter to produce a mildly acidic liquid hard surface cleaning composition of the present invention.

As used herein, "liquid compositions" mean the mildly acidic, liquid hard surface cleaning and disinfecting compositions of the present invention, or aqueous dilutions thereof.

As used herein, all parts, percentages, ppm and ratios are based on weight of the composition and assumes the materials are 100% active unless otherwise specified.

The present invention, in its product and process aspects, is described in detail as follows.

AMINE OXIDE DETERGENT SURFACTANT

The compositions comprise an amine oxide detergent surfactant which typically has a $pK_a$ of from about 4 to about 6. As described hereinafter, at least about 10% to about 100% of the amine oxide species within the composition must be in a cationic or protonated form.

The preferred liquid concentrated compositions comprise from about 0.5 to about 40 parts, preferably from about 1 to about 30 parts, more preferably from about 1 to about 25 parts, most preferably 2 parts to 16 parts of the amine oxide detergent surfactant. The concentrated liquids are diluted to provide the preferred ready to use compositions disclosed herein. The amine oxide preferably has the formula RR'R"NO, where R is a substituted or unsubstituted alkyl or alkene group containing from about 8 to about 30, preferably from about 8 to about 18 carbon atoms. Groups R' and R" are each substituted or unsubstituted alkyl or alkene groups containing from about 1 to about 18, preferably from about 1 to about 4, carbon atoms. More preferably, R' and R" are each methyl groups, examples of which include dodecyldimethyl amine oxide, tetradecyldimethyl amine oxide, hexadecyldimethyl amine oxide, octadecyldimethyl amine oxide, and coconut alkyldimnethyl amine oxides.

The amine oxide detergent surfactant can be prepared by known and conventional methods. One such method involves the oxidation of tertiary amines in the manner set forth in U.S. Pat. No. 3,223,647 and British Patent 437,566. In general terms, amine oxides are prepared by the controlled oxidation of the corresponding tertiary amines.

Examples of suitable amine oxide detergent surfactants for use in the compositions include dodecyldimethyl amine oxide, tridecyldimethyl amine oxide, tetradecyldimethyl amine oxide, pentadecyldimethyl amine oxide, hexadecyldimethyl amine oxide, heptadecyldimethyl amine oxide, octadecyldimethyl amine oxide, docecyldiethyl amine oxide, tetradecyldimethyl amine oxide, hexadecyldiethyl amine oxide, octadecyldiethyl amine oxide, dodecyldipropyl amine oxide, tetradecyldipropyl amine oxide, hexadecyldipropyl amine oxide, octadecyldipropyl amine oxide, dodecyldibutyl amine oxide, tetradecyldibutyl amine oxide, hexadecyldibutyl amine oxide, octadecyldibutyl amine oxide, dodecylmethylethyl amine oxide, tetradecylethylpropyl amine oxide, hexadecylpropylbutyl amine oxide, and octadecylmethylbutyl amine oxide.

Also useful are the amine oxide detergent surfactants which are prepared by the oxidation of tertiary amines prepared from mixed alcohol's obtainable from coconut oil. Such coconut alkyl amine oxides are preferred from an economic standpoint inasmuch as it is not necessary for the present purposes, to separate the mixed alcohol fractions into their pure components to secure the pure chain length fractions of the amine oxides.

QUATERNARY AMMONIUM DISINFECTANTS

The compositions contain water miscible quat and other substances having disinfectants properties. The key disinfectants are quaternary ammonium compounds. Examples of suitable quaternary ammonium disinfectants include dioctyl, octyldecyl and didecyldimethyl ammonium chloride, N-alkyl ($C_{12}$ to $C_{18}$) dimethyl ammonium chloride, and N-alkyl ($C_{12}$ to $C_{18}$) dimethyl ethylbenzyl ammonium chloride and mixtures thereof. These disinfectants are preferably used herein at a pH of 3 to 6.

The combinations of a quat disinfectant and the electrolytic booster provide superior disinfecting properties without the cleaning negatives, particularly the cleaning and/or staining negatives of comparable prior art compositions. The quat has a level of 50 to 1500, with a target in use level of about 600±100 ppm, but different levels of quat are useful depending on the organism against which disinfectancy is desired. Sanitizing compositions can contain at least 50 ppm quat, preferably at least 150 ppm quat. Suitable quats are disclosed in U.S. Pat. No. 5,435,935, issued to Kupneski, Jul. 25, 1995, herein incorporated by reference in its entirely.

ACIDIFYING AGENT

It was found that amine oxide staining of vinyl surfaces can be reduced or eliminated by using certain acidifying agents in the liquid composition. These acidifying agents are used to protonate a percentage of amine oxide species in the liquid composition. It was also found that these protonated or cationic amine oxides species reduce (i.e., at 10% protonation) or eliminate (i.e., at 90–100% protonation) staining thus increasing the lifetime of the vinyl surface.

The concentrated composition herein preferably comprises from 0.05 parts to 10 parts, more preferably 0.25 to 5 parts, most preferably 0.5 to 2 parts, of an acidifying agent having at least one $pK_a$ below about 6.0, preferably below about 5.0, more preferably less than 4.0, and even more preferably from about 3.0 to about 5.0. When selecting an acidifying agent, its $pK_a$ should be less than that of the selected amine oxide, preferably from about 1 to 2 units less. The acidifying agents provide for protonation of the amine oxide species in the compositions.

The acidifying agent can comprise an acid selected from organic acids, mineral acids, or mixtures thereof. Preferred mineral acids are HCl, $HNO_3$, $H_3PO_4$, $HClO_3$ and mixtures thereof. Preferred organic acids are, but not limited to, sulfosuccinic acid, methane sulfonic acid, glycerophosphoric acid, ethylenediaminetetraacetic acid (EDTA), diethylenetriaminepentaacetic acid ($H_5DTPA$), maleic acid, malonic acid, salicylic acid, tartaric acid, fumaric acid, citric acid, o-phthalic acid, malic acid, itaconic acid, lactic acid, ascorbic acid, 2,2-dimethylsuccinic acid, succinic acid, benzoic acid, and propionic acid. The acidifying agent is more preferably selected from the group of sulfosuccinic acid, citric acid, salicylic acid, phosphoric acid, nitric acid, hydrochloric acid, perchloric acid, oxalic acid, maleic acid, o-phthalic acid, and mixtures thereof. Most preferred are phosphoric acid, hydrochloric acid, nitric acid, perchloric acid, sulfosuccinic acid and mixtures thereof.

The liquid compositions contain enough of the acidifying agent to establish a composition pH of between about 3.0 and below 7.0, preferably between about 4.0 and about 6.0, more preferably between about 4.0 and about 5.5. Liquid amine oxide compositions employed on hard surfaces at a pH of less than about 3.0 can damage waxed surfaces, and when employed at a pH of 7.0 or above will cause excessive staining of vinyl surfaces.

The liquid compositions must also contain enough of the acidifying agent to protonate at least about 10% of the amine oxide species within the composition, preferably between about 50% and about 100%, more preferably between about 90% and 100%. As used herein, the term "protonated" refers to cationic amine oxide species containing a quaternary ammonium group. The protonation or conversion of nonionic to cationic amine oxides is represented generally by the reaction formula $$RR'R''N{\rightarrow}O + H^+ \rightarrow RR'R''N^+OH$$

To achieve the requisite composition pH and amine oxide protonation, the concentration of the preferred acidifying agents, i.e., the in the preferred liquid compositions will typically be between about 0.05 parts and about 10 parts, more typically between about 0.1 parts and about 7 parts by weight of the liquid concentrated compositions. Acid concentrations will vary depending on the $pK_a$ of the amine oxide, the strength ($pK_a$ and concentration) of the selected acidifying agent, the target pH of the composition, the molecular weight of the amine oxide and the acid(s) source(s) and the relative acidity/basicity of other materials in the composition. Since mineral acids tend to have lower $pK_a$ than organic acids, target pH values are more easily obtained with mineral acids. Mineral acids can be combined with weaker organic acids to more easily reach the target pH.

The liquid compositions can be used in diluted or undiluted form to clean hard surfaces. Disinfectant compositions must be registered with the EPA as pesticides so they must be used as registered to disinfect. The compositions will typically be diluted with an aqueous liquid, usually tap water, prior to use. When diluted, the compositions comprise from about 40 ppm to about 12,500, preferably from about 100 ppm to about 2800 ppm, of the amine oxide detergent surfactant. Whether diluted or undiluted, the liquid composition employed on hard surfaces must have the requisite composition pH and amine oxide protonation described herein.

The requisite pH of the composition is maintained by the amine oxide component. Amine oxide detergent surfactants normally have an adequate buffering capacity in the pH range described herein. Even when diluted with tap water, the amine oxide component can normally maintain the composition pH below 7.0. Additional buffers can be added if necessary to help maintain acidity. Such buffers are optional.

The vinyl staining described herein comes from the dehydrochlorination of polyvinyl chloride surfaces. It is believed that this dehydrochlorination reaction is accelerated by nonacidic amine oxide compositions. This accelerated dehydrochlorination is represented by the reaction formula

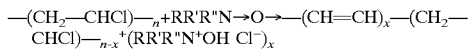

| Polyvinyl chloride Amine oxide (colorless) | Dehydrochlorinated polyvinyl chloride (yellow-brown color) |

Dehydrochlorinated polyvinyl chloride has a yellow to brown appearance, depending on the degree of dehydrochlorination. This dehydrochlorination is believed to be accelerated by nonionic amine oxide species found in nonacidic liquid hard surface cleaners. By protonating the amine oxide to the extent described herein, and by maintaining an acidic environment, the rate of dehydrochlorination is greatly reduced and vinyl staining is reduced or eliminated. In the liquid compositions herein, the protonated amine oxides cannot initiate the dehydrochlorination reaction so staining stops.

The data summarized in Table I shows that mildly acidic, liquid amine oxide compositions of the present invention cause little or no staining when used on vinyl tiles.

TABLE I

Dilute Product Vinyl Tile Staining From the Use of Liquid Amine Oxide Compositions[1]

| Composition | Coconut dimethyl amine oxide (ppm) | Acidifying agent | $pK_a$ of acidifying agent | Concentration of acidifying agent (ppm) | Composition pH | Degree of vinyl staining |
|---|---|---|---|---|---|---|
| A | 700 | none | none | none | 8.0 | severe |
| B | 700 | $H_3PO_4$ | 2.12, 7.12, 12.32 | 100 | 4.6 | none |
| C | 700 | HCl | very low | 110 | 4.7 | light |
| D | 700 | $HNO_3$ | very low | 200 | 4.7 | none |
| E | 700 | Maleic acid | 2.00, 6.26 | 150 | 4.7 | none |
| F | 700 | Oxalic acid | 1.19, 4.21 | 140 | 4.7 | light |

TABLE I-continued

Dilute Product Vinyl Tile Staining From the Use of Liquid Amine Oxide Compositions[1]

| Composition | Coconut dimethyl amine oxide (ppm) | Acidifying agent | $pK_a$ of acidifying agent | Concentration of acidifying agent (ppm) | Composition pH | Degree of vinyl staining |
|---|---|---|---|---|---|---|
| G | 700 | O-Phthalic acid | 3.10, 5.27 | 250 | 4.6 | light |
| H | 700 | Tartaric acid | 3.02, 4.54 | 230 | 4.6 | light |
| I | 700 | Citric acid | 3.06, 4.74, 5.40 | 200 | 4.6 | light |
| J | 700 | Malic acid | 3.40, 5.05 | 200 | 4.6 | light/moderate |
| K | 700 | Succinic acid | 4.19, 5.57 | 200 | 4.8 | light |
| L | 700 | Acetic acid | 4.76 | 230 | 4.9 | moderate |

[1]Each composition contained 600 ppm (didecyldimethyl ammonium chloride) surfactant.

To generate the data summarized in Table I, the following vinyl staining method are employed. This method accelerates staining but it correlates well with long term vinyl staining under normal conditions in the field. In accordance with this method, white vinyl floor tiles are rinsed with warm tap water, followed by two rinses with isopropanol before they are allowed to air dry. About 1 cc of each composition A–L is separately applied to discreet regions of the tiles. The tiles are kept at room temperature for 1 hour and then placed in an oven at 60° C. (140° F.) for 1 hour, 45 minutes. The tiles are removed from the oven and allowed to cool to room temperature. The cooled tiles are then rinsed with tap water and the treated regions on each tile are visually inspected for vinyl staining. The degree of staining is rated as "none" (no color change), "light" (very slight but noticeable discoloration), "moderate" (yellow color change) or "severe" (brown color change). Each composition A–L is a 1:128 dilution of a liquid concentrate with a pH of about 4.5. After dilution, each composition (B–L) as applied to the tiles has a pH of between about 4.5 and 5.0. Each diluted composition therefore consists of water, coconut dimethyl amine oxide, quat and a specific acidifying agent.

Composition A is the control product. It has a pH of about 8.0. Essentially 100% of the amine oxide surfactant is therefore in nonionic form. This composition (A) causes severe staining.

Compositions B–J were mildly acidic amine oxide compositions where 90–100% of the amine oxide species are protonated with acidifying agents having $pK_a$ values below about 3.0. Compositions B–L caused little or no vinyl staining.

Compositions K & L contain weaker acids ($pK_a$ values above about 3.0) which causes only light to moderate staining. Note however, that all of the mildly acidic compositions (B–L) cause significantly less staining than composition A which has a much higher pH (8.0) and therefore has less than 10% of its amine oxide species in cationic form.

DISINFECTANCY vs. pH and AO PROTONATION

It has been found that under acidic conditions, protonated amine oxides limit quat disinfectancy on gram positive (i.e., Staphylococci) bacteria. Without being bound by theory, it is believed that protonated amine oxides (cationic) compete for binding sites on the cell wall with the quat (cationic) disinfectants. Quats are bactericidal because they destroy the integrity of the cell membrane by disrupting the interactions between the membrane proteins and lipids. Since the surface of the bacterium is normally negatively charged this helps attract and bind quat (positively charged) disinfectants. Since the protonated amine oxide (AOH+) is also cationic, the quat and the $AOH^+$ compete for the same binding sites. AOHe has little or no inherent bactericidal activity so the overall disinfectancy of the mixture is reduced dramatically (see Table II). The formulations M–Q in Table II are based on the one described in Comparative Example 4. No EDTA or KCl are in formulations M-Q. The pH's of N–Q are adjusted by adding phosphoric acid.

TABLE II pH/Amine Oxide/Protonated Amine Oxide/Quat Disinfectancy Testing

| # | Solution pH | % AOH | % $AOH^+$ | Disinfectancy Results[1] |
|---|---|---|---|---|
| M | 8.0 | 100 | 0 | 0/10 (Pass) |
| N | 7.0 | 100 | 0 | 0/10 (Pass) |
| O | 6.0 | 97 | 3 | 2/10 (Fail) |
| P | 5.0 | 76 | 24 | 6/10 (Fail) |
| Q | 4.0 | 24 | 76 | 10/10 (Fail) |

[1]The Environmental Protection Agency (EPA) measures disinfectant efficacy using the AOAC Use-Dilution Method. In a test, test tube carriers are inoculated with the bacterium of interest (*Staphylococcus aureus* in this example) and it is then treated with the test product. After a fixed incubation period, the carriers are evaluated for the presence of live bacteria. Results are reported as the number of tubes showing growth/total number of tubes inoculated. The data reported in Table II is a screening test because only 10 tubes are inoculated. Results of 0/10 indicate no bacteria growth in the 10 tubes tested (pass); 10/10 indicates growth in all 10 tubes (failure). In a screening test, any growth is considered a failure. To register a formula as a disinfectant, 60 carriers must be inoculated and bacteria growth cannot be noted in more than 1 tube.

While not being bound by theory, we believe that the protonated amine oxide ($AOH^+$) is not bactericidal because it either cannot pass through the cell wall because of its chemical structure or that the interstitial pH (>7) of the cell quickly deprotonates the amine oxide rendering it ineffective.

ELECTROLYTIC DISINFECTING BOOSTER

The compositions of the present invention include an effective amount of an electrolytic disinfecting booster comprising an alkali or alkaline earth metal salt wherein the anion is selected from the group consisting of halides, nitrates, sulfate, and perchlorate. Preferred are salts selected from the group consisting of: LiCl, LiBr, $LiNO_3$, NaCl, NaBr, NaI, KCI, KBr, KI, $KNO_3$, $KClO_4$, $CaCl_2$, $BaCl_2$, $Na_2SO_4$, $MgSO_4$ and mixtures thereof The level of the booster in the concentrate is from 0.05 to 12 parts, preferably 0.2 to 8 parts. Lower levels are preferred. The level of the booster in the ready to use compositions are preferably 15 ppm to 500 ppm, more preferably 25 ppm to 300 ppm. The electrolytic disinfecting booster surprisingly increases the disinfectancy of the composition. The more preferred boosters are strong electrolytes, especially, KCl and NaCl.

AQUEOUS CARRIER LIQUID

The compositions herein are employed on hard surfaces in liquid form. Accordingly, the foregoing components are admixed with an aqueous carrier liquid. The choice of aqueous carrier liquid is not critical. It must be safe and it must be chemically compatible with the components of the compositions. It should be either neutral or acidic to minimize the amount of acidifying agent needed.

The aqueous carrier liquid can comprise solvents commonly used in hard surface cleaning compositions. Such solvents must be compatible with the components of the compositions and must be chemically stable at the mildly acidic pH of the compositions. They should also have good filming/residue properties. Solvents for use in hard surface cleaners are described, for example, in U.S. Pat. No. 5,108,660, issued to Michael, 1992, which is incorporated herein by reference.

Preferably, the aqueous carrier liquid is water or a miscible mixture of alcohol and water. Water-alcohol mixtures are preferred inasmuch as the alcohol can aid in the dispersion and dissolution of the amine oxide and other materials in the compositions. Moreover, the alcohol can be used to adjust the viscosity of the compositions. The alcohol's are preferably $C_2$–$C_4$ alcohol's. Ethanol is most preferred.

Most preferably, the aqueous carrier liquid is water or a water-ethanol mixture containing from about 0 parts to about 50 parts ethanol.

NON-LIQUID FORMULATION

The present invention also embodies a non-liquid composition from which the mildly acidic, liquid hard surface cleaning compositions can easily be obtained by adding an aqueous carrier liquid. The non-liquid compositions can be in granular, powder or gel forms, preferably in granular forms.

The non-liquid compositions generally comprise the higher levels of the component of the composition described herein except for the aqueous carrier.

The non-liquid compositions also comprise an acidifying agent as described herein, preferably an organic acidifying agent. The non-liquid compositions contain enough of the acid to provide, upon dilution with the aqueous carrier liquid, a pH and percent amine oxide protonation within the ranges described herein for the mildly acidic, liquid compositions.

The non-liquid gel compositions contain reduced amounts of the aqueous carrier liquid. The non-liquid granular compositions contain substantially no aqueous carrier liquid. In either form, an aqueous carrier liquid is added to the liquid composition prior to use to form the mildly acidic, liquid hard surface cleaning compositions of the present invention.

AUXILIARY MATERIALS

Optionally, the compositions herein can contain auxiliary materials which augment cleaning and aesthetics.

The compositions can optionally comprise a non-interfering auxiliary surfactant in addition to the amine oxide detergent surfactant. Additional auxiliary surfactants can effect cleaning activity. A wide variety of organic, water soluble surfactants can optionally be employed. The choice of auxiliary surfactant depends on the desires of the user with regard to the intended purpose of the compositions and the commercial availability of the surfactant.

The compositions can contain any of the nonionic and zwitterionic/amphoteric surfactants commonly employed in liquid hard surface cleaning compositions.

Examples of compatible auxiliary surfactants useful in the compositions are set forth below. The term "alkyl" used to describe these various surfactants encompasses the hydrocarbyl alkyl groups having a chain length of from about $C_8$ to $C_{22}$, i.e., materials of the type generally recognized for use as detergents. Examples of suitable nonionic surfactants include the polyethoxysorbitan esters, fatty acyl mono- and di-ethanol amides, $C_8$–$C_{22}$ ethoxylates and mixed coconut ethoxylates containing 1 to 30 ethoxylate groups.

Examples of suitable zwitterionic surfactants include the fatty alkyl betaines and sulfobetaines and similar compounds such as Cg to $C_{18}$ amino propane sulfonate and $C_8$ to $C_{18}$ hydroxy ammonium propane sulfonates.

In general, anionic surfactants cannot be used in sufficient quantity to provide a cleaning benefit. Anionic (negatively charged) surfactants can combine with the cationic (positively charged) disinfectant quat and/or $AOH^+$ to form an insoluble precipitate. However, low levels of anionic surfactants (<5%) can be used to adjust physical properties like specific gravity and viscosity without precipitating the quat disinfectant or $AOH^+$. For most purposes, it is preferred to use the anionic materials in their acid form to reduce the amount of auxiliary acid needed to acidic the composition. Especially preferred anionic surfactants herein are the linear alkyl benzene sulfonates and the alkyl ether sulfates of the general formula $AE_xSO_4$ wherein $A=C_{10}$–$C_{22}$ alkyl, E is ethylene oxide, and wherein x is an integer from 0 to 30; the $C_{10}$–$C_{14}$ olefin sulfonates, and mixtures thereof Other optional additives such as perfumes, brighteners, enzymes, colorants, and the like can be employed in the compositions to enhance aesthetics and/or cleaning performance.

Detergent builders can also be employed in the compositions. These builders are especially useful when auxiliary surfactants or cosurfactants are employed, and are even more useful when the compositions are diluted prior to use with exceptionally hard tap water., e.g., above about 12 grains. Detergent builders sequester calcium and magnesium hardness ions that might otherwise bind with and render less effective the auxiliary surfactants or cosurfactants. The detergent builders can be employed in the compositions at concentrations of between about 0 parts and about 10 parts.

Alkaline builder materials are not typically useful herein since they may not be effective under acidic conditions. Instead, the optional builder materials should comprise acidic or neutral sequestrants and include, for example, water soluble polycarboxylic acids (e.g., acrylic and maleic acid polymers and copolymers), polysulfonic acids, aminopolyacetic acids, and the like.

Suds suppressors are especially useful in the composition. In the hard surface cleaning composition herein, suds formation and maintenance are undesirably promoted by the amine oxide component. The compositions therefore preferably comprise a sufficient amount of a suds suppresser to prevent excessive sudsing during employment of the compositions on hard surfaces. Suds suppressors are especially useful to allow for no-rinse application of the composition.

The suds suppresser can be provided by known and conventional means. Selection of the suds suppresser depends on its ability to formulate in the compositions, and the residue and cleaning profile of the compositions. The suds suppresser must be chemically compatible with the components in the compositions, it must be functional at the pH range described herein, and it should not leave a visible residue on cleaned surfaces.

Low-foaming cosurfactants can be used as suds suppresser to mediate the suds profile in the compositions. Cosurfactant concentrations between about 1 part and about 3 parts are normally sufficient. Examples of suitable cosurfactants for use herein include block copolymers (e.g., Pluronic® and Tetronic®, both available from BASF Company) and alkylated (e.g., ethoxylated/propoxylated) primary and secondary alcohols (e.g., Tergitol®, available from Union carbide; Poly-Tergent®, available from Olin Corporation).

The optional suds suppressor preferably comprises a silicone-based material. These materials are effective as suds suppressors at very low concentrations. The compositions preferably comprise from about 0.01 parts to about 0.50 parts, more preferably from about 0.01 parts to about 0.3 parts of the silicone-based suds suppresser. At these low concentrations, the silicone-based suds suppresser is less likely to interfere with the cleaning performance of the compositions. An example of suitable silicone-based suds suppressors for use in the compositions is Dow Corning® DSE. These optional but preferred silicone-based suds suppressors can be incorporated into the composition by known and conventional means.

BENEFITS

In addition to their reduced vinyl staining described hereinbefore, the compositions also have surprisingly superior cleaning and disinfecting properties and leave little or no visible residue on hard surfaces when they dry. The composition of this invention can be used for cleaning and disinfecting toilets, etc., as well as hard surfaces.

It was found that these compositions leave surprisingly little or no visible residue on hard surfaces whether used in a rinse or no-rinse application. They are also surprisingly wax compatible. As described hereinbefore, at least about 10% of the amine oxide species in the composition are cationic. Cationic surfactants, however, tend to form crystalline salts upon drying thus resulting in cloudy residues. This does not occur, however, with the application (rinse or no-rinse application) of the instant compositions to hard surfaces.

It was also found that the compositions exhibit excellent particulate and greasy soil removal properties. This was surprising since acidic liquid hard surface cleaners do not typically clean particulate or greasy soil from hard surfaces as well as non-acidic hard surface cleaners do. Acidic hard surface cleaners are used mostly in bathrooms to remove hard water stains.

The compositions provide excellent soil removal properties while leaving little or no visible residue on cleaned surfaces with little or no notable damage as with the state of art products. Hard surface cleaners typically have either good soil removal properties or good residue properties (e.g., they do not leave a visible residue on cleaned surfaces), but not both. The compositions herein provide both of these desirable properties in a single product. It is therefore uniquely suited to clean, for example, heavily soiled shiny surfaces, e.g., waxed vinyl floors.

METHOD OF USE

The present invention has been fully set forth in its composition aspects. The invention also encompasses a method for cleaning and disinfecting vinyl surfaces (waxed or unwaxed). The benefit of using this composition on vinyl surfaces is described hereinbefore.

The method comprises applying to a vinyl surface the mildly acidic liquid compositions herein or, preferably, applying an aqueous dilution thereof. The vinyl surface is then wiped with a porous material, e.g., cloth or mop, and allowed to dry.

In a preferred method, the mildly acidic composition is first diluted with an aqueous liquid, preferably tap water. The diluted composition has a pH of between about 3.0 and below 7.0, preferably between about 4.0 and about 6.0, and comprises from about 40 ppm to about 12,500 ppm, preferably from about 100 ppm to about 2800 ppm, of the amine oxide detergent surfactant described herein and has quat at a level of about 600 ppm. At least about 10% of the amine oxide species in the diluted composition are protonated, preferably from about 50% to about 1000%, more preferably from about 90% to about 100%. The diluted composition is then applied to and wiped over (with a porous material) the vinyl surface and allowed to dry.

In a preferred method (see the Examples herein), the mildly acidic concentrated composition of this invention is first diluted with an aqueous liquid, preferably tap water. The concentrated compositions contain from 0.05 to 10 parts of an acidifying agent to protonate the amine oxide and provide the desired pH. The diluted composition has a pH of between about 3.0 and 7.0, preferably between about 4.0 and about 6.0, and comprises from about 40 to 12,500, preferably 200 ppm to about 2000 ppm, more preferably from about 400 ppm to about 1000 ppm, of the amine oxide detergent surfactant described herein; and has a disinfecting quat at a level of about 600±100 ppm. At least about 10% of the amine oxide species in the diluted composition are protonated, preferably from about 50% to about 100%, more preferably from about 90% to about 100%. The preferred compositions contain a strong electrolyte, e.g., KCl, at a level of 15 ppm to 500 ppm. The diluted composition is then applied to and wiped over (with a porous material) the vinyl surface and allowed to dry.

EXAMPLES

The following examples illustrate the compositions of the present invention, but are not intended to be limiting thereof.

Example 1 is prepared by mixing the ingredients in no particular order to form a concentrated composition. The concentrated composition is diluted with tap water on a 1:128 by volume dilution level and tested for cleaning and disinfecting. The dilute composition of Example 1 is effective against both gram positive and gram negative organisms. The pH of the concentrated composition is 4.5. The pH of the dilute composition will be about 4.5 to 5.

Example 1

| | |
|---|---|
| Amine Oxide‡ | 9.00 |
| Quaternary Ammonium† | 7.68 |
| H$_4$EDTA | 2.00 |
| Phosphoric Acid | 1.11 |
| Ethanol$^a$ | 0.96 |
| Potassium Chloride | 0.95 |
| Maleic Acid$^a$ | 0.56 |
| Poly-tergent CS-1 LP* | 0.50 |
| Perfume | 0.40 |
| Na$_5$DTPA$^a$ | 0.17 |
| Silicone Solids (D.C. DSE) | 0.0064 |

-continued

| | |
|---|---|
| H₂O₂ᵃ | 0.04 |
| Water, Color & Misc. | 76.55 |
| | 100.00% |

‡coconut dimethyl amine oxide
†Didecyl Dimethyl Ammonium Chloride
*Ethoxylated and propoxylated surfactants
ᵃRaw material by-products The ppm by volume for the diluted ready to use compositions is calculated for this Example by multiplying the parts by 10,000÷128.

Some preferred variation of the composition of this Example 1 comprises: about 8 to 10 parts amine oxide surfactants; about 6–8 parts quaternary ammonium chloride; about 1–3 parts EDTA; about 0.5 to 1.2 parts phosphoric acid; about 0.5 to 1.25 potassium chloride; and balance water. The pH is preferably adjusted with HCl or phosphoric acid or mixtures thereof. All variations kill gram positive and gram negate organism.

Example 2

The same as Example 1 except that the acid EDTA is replaced with more acid, e.g., with more phosphoric acid. This composition cleans well but does not disinfect against gram negative organisms but is effective against gram positive organisms.

Comparative Example 3

The same as Example 1 except that the potassium chloride is removed. This composition cleans well, but is not effective on gram positive organisms.

Comparative Example 4

This Example is the same as Comparative Example 3 except that EDTA is also removed. Comparative Example 4 is not effective on gram positive or gram negative organisms at pH's below 7. (See Table II.)

What is claimed is:

1. Liquid cleaning compositions comprising: an amine oxide detergent; a quaternary disinfectant (quat); an acidifying agent; an effective amount of an electrolytic disinfecting booster and an aqueous carrier; wherein said cleaning compositions have an acidic pH of from 3 to less than 7; and from 40 parts per million (ppm) to 12,500 ppm of said amine oxide detergent; and from 50 ppm to 1500 ppm of said quat; wherein said electrolytic disinfecting booster is an inorganic alkali or alkali earth metal salt wherein the anion of said salt is selected from the group consisting of halides, nitrate, sulfate, and perchlorate.

2. The compositions according to claim 1 wherein said electrolytic disinfecting booster is selected from the group consisting of NaCl, NaBr, NaI, KCl, KBr, KI and mixtures thereof; and wherein the level of said electrolytic disinfecting booster is from 15 ppm to 500 ppm.

3. The cleaning compositions according to claim 1 wherein the acidifying agent is selected from the group consisting of: ethylenediamine tetracetic acid (EDTA), perchloric acid and sulfosuccinic acid; wherein the electrolytic disinfecting booster is selected from NaCl and KCl and mixtures thereof.

4. The cleaning compositions according to claim 1, wherein said cleaning compositions comprise from 100 to 2800 ppm, of the amine oxide detergent; wherein the pH of the liquid compositions is from 4 and 6, and from 90% and 100% of the amine oxide detergent is protonated; wherein said quaternary disinfectant is selected from the group consisting of: dioctyl, octyldecyl and didecyl dimethyl ammonium chloride, N-alkyl ($C_{12}$ to $C_{18}$) dimethyl ammonium chloride, and N-alkyl ($C_{12}$ to $C_{18}$) dimethyl ethylbenzyl ammonium chloride and mixtures thereof.

5. A method for cleaning and sanitizing or disinfecting vinyl surfaces, which method comprises the steps of:
   a) applying the ready to use liquid cleaning compositions of claim 1 to a vinyl surface; and then
   b) wiping the liquid cleaning compositions over the vinyl surface with a porous material and allowing said vinyl surface to dry.

6. A method according to claim 5 wherein the liquid cleaning compositions have a pH of between 4 and 6, the acidifying agent has a $pK_a$ of less than 4.0, and between 90% and 100% of the amine oxide detergent within the liquid cleaning compositions are protonated.

7. Non-liquid concentrated hard surface cleaning compositions which upon dilution with water provide the cleaning compositions of claim 1.

8. A concentrated hard surface cleaning composition comprising:
   (a) from 0.5 to 40 parts of an amine oxide detergent surfactant;
   (b) from 1 to 25 parts of a quaternary disinfectant;
   (c) from 0.05 parts to 10 parts of an acidifying agent having a $pK_a$ of less than about 6.0; and
   (d) from 0.05 to 12 parts of an electrolytic disinfecting booster wherein said booster is an inorganic alkali or alkali earth metal salt wherein the anion of said salt is selected from the group consisting of halides, nitrates, sulfate, and perchlorate;
wherein said concentrated cleaning composition when diluted with water at a ratio level of concentrate to water of from 1:1 to 1:600 by volume provide a ready to use cleaning and disinfecting composition.

9. The concentrated hard surface clearing compositions of claim 8, wherein said concentrated cleaning compositions comprises:
   a) from 1 to 25 parts said amine oxide detergent;
   b) from 2 parts to 16 parts said quaternary disinfectant;
   c) optionally 1–3 parts of ethylenediamine tetracetic acid (EDTA);
   d) from 0.25 parts to 2.0 parts of phosphoric acid;
   e) from 0.2 to 2 parts of said electrolytic disinfecting booster,
   f) balance water; and
wherein said concentrated cleaning compositions when diluted with water at a ratio level of concentrate to water of from 1:30 to 1:260 by volume provide ready to use cleaning and disinfecting compositions.

10. The concentrated hard surface cleaning compositions of claim 9, wherein said concentrated cleaning compositions comprise:
   a) from 8 to 10 parts said amine oxide detergent;
   b) from 6 to 8 parts said quaternary disinfectant;
   c) from 1 to 3 parts of ethylenediamine tetracetic acid (EDTA);
   d) from 0.5 to 1.2 parts of phosphoric acid;
   e) from 0.5 to 1.25 parts of said potassium chloride;
   f) balance water; and
wherein said concentrated cleaning compositions are diluted with water by 1:128 to provide a ready to use dilute composition.

11. The composition according to claim 1 wherein said electrolytic disinfecting booster is selected from the group consisting of LiCl, LiBr, LiNO$_3$, NaCl, NaBr, NaI, KCl, KBr, KI, KNO$_3$, KClO$_4$, CaCl$_2$, BaCl$_2$, Na$_2$SO$_4$, MgSO$_4$, and mixtures thereof.

12. The composition according to claim 2 wherein the level of said electrolytic disinfecting booster is from 25 to 300 ppm; and wherein said pH is from 4 to 5.

13. The composition according to claim 3 wherein said amine oxide detergent has the formula RR'R"NO, where R contains from 8 to 30 carbon atoms, and R' and R" each contain from 1 to 18 carbon atoms.

14. The composition according to claim 4 wherein said composition comprises from 200 ppm to 2000 ppm of said amine oxide detergent; wherein said composition further comprises a suds suppressor; and wherein said quaternary disinfectant is didecyl dimethyl ammonium chloride.

15. The composition according to claim 6 wherein said amine oxide detergent has the formula RR'R"NO, where R contains from 8 to 18 carbon atoms, and R' and R" each contain from 1 to 4 carbon atoms.

16. The composition according to claim 9 wherein said quaternary disinfectant is quaternary ammonium chloride; and wherein said electrolytic disinfecting booster is potassium chloride.

17. The composition according to claim 10 wherein said quaternary disinfectant is quaternary ammonium chloride.

* * * * *